United States Patent
Shuros et al.

(10) Patent No.: US 8,412,325 B2
(45) Date of Patent: Apr. 2, 2013

(54) HIGH-ENERGY ANTI-TACHYCARDIA THERAPY

(75) Inventors: Allan Charles Shuros, St. Paul, MN (US); Shantha Arcot-Krishnamurthy, Vadnais Heights, MN (US); Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 51 days.

(21) Appl. No.: 12/419,074

(22) Filed: Apr. 6, 2009

(65) Prior Publication Data

US 2009/0254135 A1    Oct. 8, 2009

Related U.S. Application Data

(60) Provisional application No. 61/043,263, filed on Apr. 8, 2008.

(51) Int. Cl.
*A61N 1/362* (2006.01)
(52) U.S. Cl. ............... 607/14; 607/4; 607/9; 607/15
(58) Field of Classification Search .......... 607/4, 5, 607/9, 11, 14, 15
See application file for complete search history.

(56) References Cited

U.S. PATENT DOCUMENTS

| | | | |
|---|---|---|---|
| 4,520,825 A * | 6/1985 | Thompson et al. ............ | 607/59 |
| 4,869,252 A | 9/1989 | Gilli | |
| 5,184,616 A | 2/1993 | Weiss | |
| 5,301,677 A | 4/1994 | Hsung | |
| 5,531,764 A | 7/1996 | Adams et al. | |
| 5,978,707 A | 11/1999 | Krig et al. | |
| 6,317,631 B1 | 11/2001 | Ben-Haim et al. | |
| 6,658,286 B2 | 12/2003 | Seim | |
| 6,711,442 B1 * | 3/2004 | Swerdlow et al. ............ | 607/63 |
| 6,751,501 B1 | 6/2004 | Schuler et al. | |
| 6,856,835 B2 | 2/2005 | Bardy et al. | |
| 6,892,094 B2 * | 5/2005 | Ousdigian et al. ............ | 607/4 |
| 6,952,610 B2 | 10/2005 | Ostroff et al. | |
| 7,151,962 B2 | 12/2006 | Belk | |
| 7,162,299 B1 | 1/2007 | Kroll et al. | |
| 7,225,017 B1 | 5/2007 | Shelchuk | |

(Continued)

FOREIGN PATENT DOCUMENTS

| | | |
|---|---|---|
| EP | 0253505 | 1/1988 |
| WO | 9740886 | 11/1997 |

OTHER PUBLICATIONS

*Tachyarrhythmia Therapy, System Guide*, Guidant Corporation, Ch. 4-8 through 4-18, (2008).

(Continued)

*Primary Examiner* — Carl H Layno
*Assistant Examiner* — Eugene Wu
(74) *Attorney, Agent, or Firm* — Pauly, DeVries Smith & Deffner, L.L.C.

(57) ABSTRACT

Embodiments of the invention are related to medical devices and methods for delivery high-energy anti-tachycardia therapy to a subject, amongst other things. In an embodiment, the invention includes a medical device including a controller module configured to administer a plurality of electrical pulses to a patient in response to a detected tachycardia, the electrical pulses comprising an amplitude of greater than 3 Volts and less than 40 Volts, the controller configured to modulate the amplitude of the electrical pulses. In an embodiment, the invention includes a method of treating a tachyarrhythmia including administering a first series of electrical pulses to a patient with an implantable medical device, the electrical pulses including an amplitude of greater than 8 Volts and less than 40 Volts, the first series of electrical pulses having an interval of less than about 600 ms in between individual pulses. Other embodiments are also included herein.

16 Claims, 11 Drawing Sheets

U.S. PATENT DOCUMENTS

| | | | |
|---|---|---|---|
| 7,596,410 B1 * | 9/2009 | Kroll et al. | 607/14 |
| 2002/0035376 A1 | 3/2002 | Bardy et al. | |
| 2004/0049235 A1 | 3/2004 | Deno et al. | |
| 2004/0210257 A1 * | 10/2004 | Havel et al. | 607/5 |
| 2005/0137637 A1 * | 6/2005 | Bardy et al. | 607/27 |
| 2006/0074331 A1 | 4/2006 | Kim et al. | |
| 2006/0161069 A1 | 7/2006 | Li | |

OTHER PUBLICATIONS

Batsford, "Pacemakers and Antitachycardia Devices", *Yale University School of Medicine Heart Book*, Ch. 26, pp. 331-338 (1992).

Gulizia, et al., "Randomized comparison between Ramp and Burst+ atrial antitachycardia pacing therapies in patients suffering from sinus node disease and atrial fibrillation and implanted with a DDDRP device", *Europace*, 8:465-473 (2006).

Hook, et al., "Acute and Chronic Cycle Length Dependent Increase in Ventricular Pacing Threshold", *PACE*, 15:1437-1444 (1992).

Schaumann, et al., "Empirical Versus Tested Antitachycardia Pacing in Implantable Cardioverter Defibrillators: A Prospective Study Including 200 Patients", *Circulation*, 97:66-74 (1998).

Wathen, et al., "Shock Reduction Using Antitachycardia Pacing for Spontaneous Rapid Ventricular Tachycardia in Patients With Coronary Artery Disease", *Circulation*, 104:796-801 (2001).

PCT International Search Report and Written Opinion, mailed Aug. 8, 2011, from International Application No. PCT/US2009/039798, corresponding to U.S. Appl. No. 12/419,074, pp. 1-14.

PCT Notification Concerning Transmittal of International Preliminary Report on Patentability, mailed Sep. 1, 2011, from International Application No. PCT/US2009/039798, corresponding to U.S. Appl. No. 12/419,074, pp. 1-9.

US 5,584,866, 12/1996, Kroll et al. (withdrawn)

\* cited by examiner

HIGH-ENERGY ANTI-TACHYCARDIA THERAPY

This application claims the benefit of U.S. Provisional Application No. 61/043,263, filed Apr. 8, 2008, the content of which is herein incorporated by reference.

TECHNICAL FIELD

This disclosure relates generally to medical devices and methods for delivery of therapy to a subject, and more particularly, to medical devices and methods for delivery of high-energy anti-tachycardia therapy to a subject, amongst other things.

BACKGROUND OF THE INVENTION

Tachycardia is a heart condition defined in an adult as a heart rate faster than 100 beats/minute. Tachycardia can broadly be classified as either sinus tachycardia, supraventricular tachycardia, or ventricular tachycardia. Sinus tachycardia is generally caused by exercise or emotional stress and is generally normal. Supraventricular tachycardia is defined as a tachycardia that originates above the bifurcation of the bundle of His. Ventricular tachycardia is defined as a tachycardia that originates below the bifurcation of the bundle of His. Some tachycardias are normal while others can have serious consequences including dramatically reducing cardiac output leading to chest pain, syncope, and death. As such, it is important to treat tachycardia appropriately.

Implantable medical devices are commonly used to treat patients with various conditions of the heart including tachycardias. In some cases, an implantable device is used to deliver a high-energy defibrillation or cardioversion shock to a patient's heart. Such shocks are generally successful at terminating tachycardias. However, defibrillation and cardioversion shocks cause extreme discomfort for patients.

Anti-tachycardia pacing (ATP) was developed as another implantable device-based technique for terminating tachyarrhythmias. ATP generally includes the delivery of a series of low-voltage pulses at a very rapid rate. These low-voltage pulses are generally delivered at the same voltage as regular pacing pulses used for treatment of bradycardia. Typically the initial interval between ATP pacing pulses is 80% of the R-R interval of the tachyarrhythmia to be treated. As such, the ATP pacing pulses are delivered at a rate that is faster than the tachyarrhythmia rate. ATP is effective in terminating some types of tachyarrhythmias. However, a need remains for additional techniques of terminating tachyarrhythmias.

SUMMARY OF THE INVENTION

Embodiments of the invention are related to medical devices and methods for delivery of high-energy anti-tachycardia therapy to a subject, amongst other things. In an embodiment, the invention includes a medical device including a controller module configured to administer a plurality of electrical pulses to a patient in response to a detected tachycardia, the electrical pulses comprising an amplitude of greater than 3 Volts and less than 40 Volts, the controller configured to modulate the amplitude of the electrical pulses.

In an embodiment, the invention includes a method of treating a tachyarrhythmia including administering a first series of electrical pulses to a patient with an implantable medical device, the electrical pulses including an amplitude of greater than 8 Volts and less than 40 Volts, the first series of electrical pulses having an interval of less than about 600 ms in between individual pulses.

In an embodiment, the invention includes a method of treating a patient including monitoring the patient for indicators of tachyarrhythmia; administering a first series of electrical pulses at a voltage less than or equal to 8 Volts; assessing whether or not the tachyarrhythmia has been terminated; and administering a second series of electrical pulses at a voltage greater than 8 Volts if the tachyarrhythmia has not been terminated.

In an embodiment, the invention includes a medical device including a controller module configured to administer a series of electrical pulses to a patient, the electrical pulses including an amplitude of greater than 8 Volts and less than 40 Volts, the first series of electrical pulses having an interval of less than about 600 ms in between individual pulses.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Various embodiments of the invention can include the delivery of rapid electrical pulses at a relatively high amplitude. The amplitude of the electrical pulses can be high relative to the amplitude of normal pacing pulses, but significantly low relative to defibrillation or cardioversion shocks and thus painless. It is believed that by increasing the amplitude of the pulses, it is possible to increase the effective size of the tissue being stimulated, thereby increasing the likelihood that the tissue associated with the reentrant circuit will be captured leading to more effective termination of tachyarrhythmias. In addition, it is believed that pacing at amplitudes greater than that at which traditional anti-tachycardia pacing is delivered can have positive ionotropic effects, and thus can beneficially increase in cardiac output. In multiple embodiments herein, the amplitude of pulses can be modulated or varied with respect to the programmed amplitude for regular pacing pulses in a cardiac rhythm management device. Various aspects of exemplary embodiments will now be described in greater detail.

Figure 1:
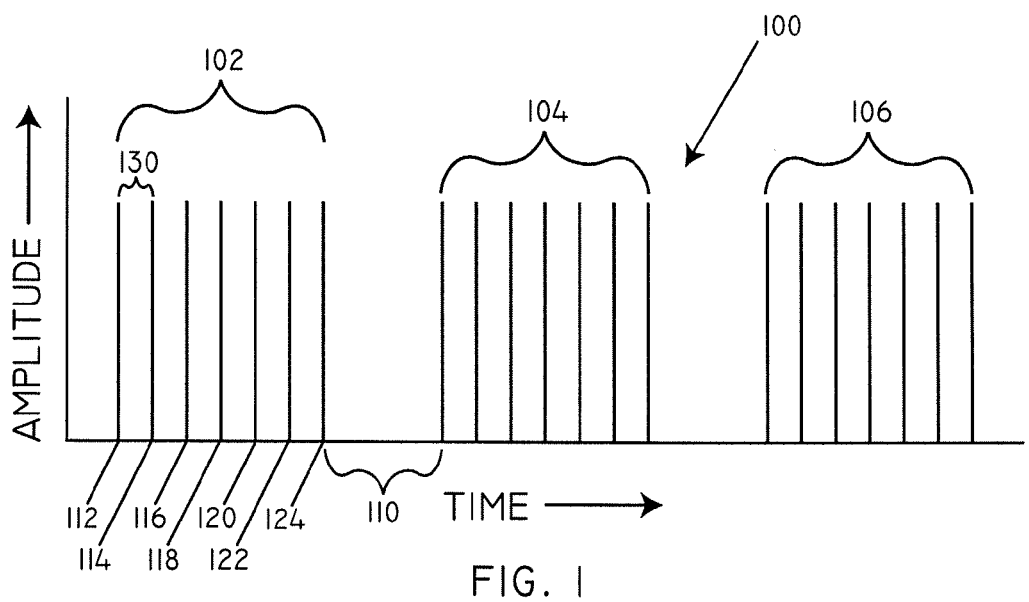
FIG. 1 is a schematic view of several series of high energy antitachycardia pacing pulses in accordance with an embodiment of the invention.

Referring now to FIG. 1, several series of high energy antitachycardia pulses in accordance with an embodiment of the invention are depicted schematically. As shown in FIG. 1, high energy antitachycardia pulses 100 are delivered as sequential, individual pulses, such as individual pulse 112. These individual pulses, e.g., 112, are grouped into a series or "pulse train", where each series consists of more than one individual pulse. For example, FIG. 1 depicts three series 102, 104, 106, where first series 102 consists of seven individual pulses 112, 114, 116, 118, 120, 122, 124. Second series 104 and third series 106 are similar to first series 102. The number of individual pulses within a series generally varies between three and eight. However, other arrangements are usable. For example, the number of individual pulses within a series and the number of series may be varied.

Each individual pulse, e.g., 112, is characterized by an amplitude, as is depicted in FIG. 1, where the amplitude of a pulse can be expressed as the electrical potential or voltage of the pulse. In general, the amplitude of a pulse is between 3 and 40 Volts. In some embodiments, the amplitude of each individual pulse is between 8 and 40 Volts. In some embodiments, the amplitude of each individual pulse is between 10 and 30 Volts. It will be appreciated that voltage, current, and resistance are all related through Ohm's law (V=I*R). As such, even though pulse amplitude modulation is discussed herein with reference to voltage, it will be appreciated that modulation of current amplitude can be included within the scope of modulating the amplitude of electrical pulses as discussed herein.

In addition, each individual pulse occurs at a particular point in time. The time at which a pulse occurs can be characterized by a time interval 130 between individual pulses. As shown in the embodiment of FIG. 1, the time interval 130 between individual pulses within a particular series may be constant. However, in other embodiments, the time interval 130 between individual pulses within a particular series may be variable. The interval between individual pulses is generally less than 600 ms. Furthermore, there is a time interval 110 between series of pulses. This time interval 110 is generally longer than time interval 130.

At least some of the individual pulses can be non-excitatory based on the timing of their delivery and/or their polarity. For example, in some embodiments, some or all of the pulses can be timed to be delivered during the refractory period.

Figure 2:
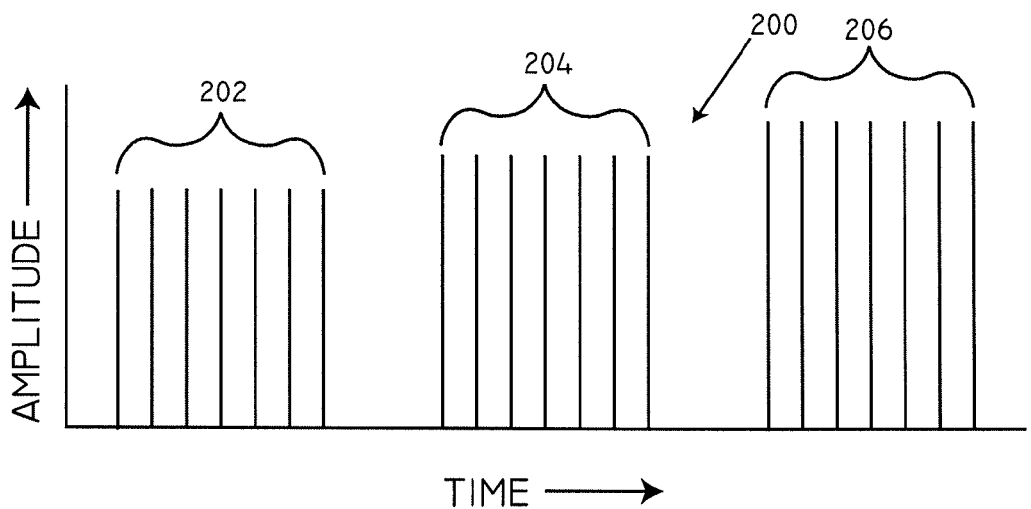
FIG. 2 is a schematic view of several series of high energy antitachycardia pacing pulses in accordance with another embodiment of the invention.

In some embodiments, the amplitude of each individual pulse is constant within a particular series, but the amplitude of the individual pulses varies from one series to another. For example, in the embodiment depicted in FIG. 2, first series 202 consists of individual pulses of a particular amplitude, while second series 204 consists of individual pulses having a greater amplitude than that of the pulses of first series 202, and where third series 206 consists of individual pulses having a greater amplitude than the pulses of second series 204. In various embodiments, the amplitude of individual pulses may increase, decrease, or alternately increase and decrease from one series to the next.

Figure 3:
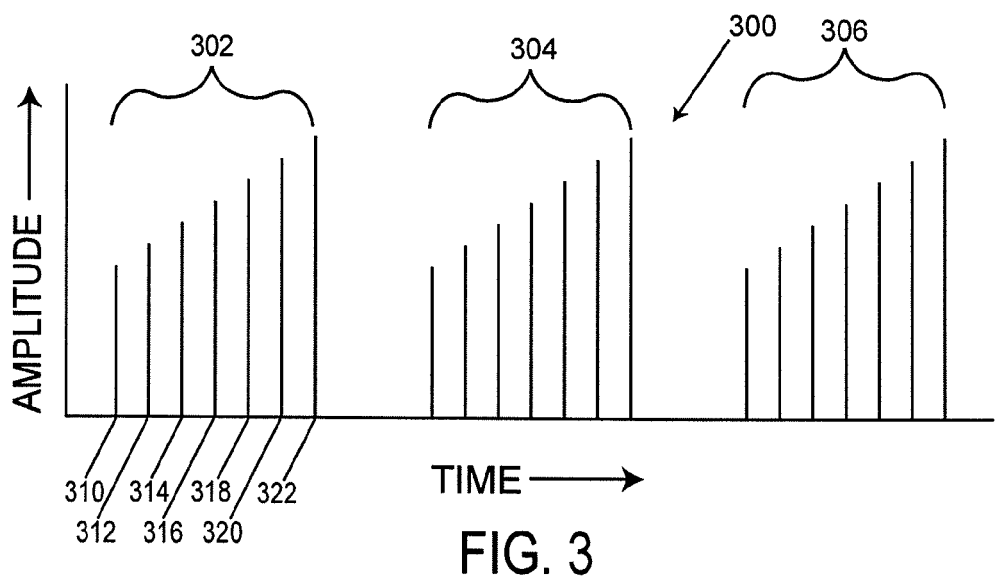
FIG. 3 is a schematic view of several series of high energy antitachycardia pacing pulses in accordance with another embodiment of the invention.
Figure 4:
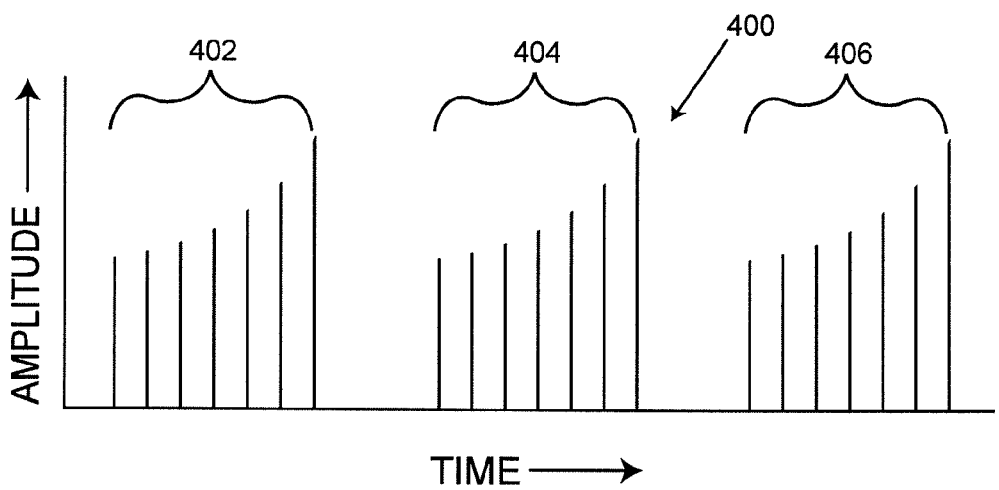
FIG. 4 is a schematic view of several series of high energy antitachycardia pacing pulses in accordance with another embodiment of the invention.

In another embodiment, the amplitude of each individual pulse varies within a series. For example, in the pulses 300 shown in the embodiment depicted in FIG. 3, the first series 302 consists of a first individual pulse 310, a second individual pulse 312 having an amplitude greater than the first individual pulse 310, and so forth, such that each of sequential individual pulses 312, 314, 316, 318, 320, 322 has a greater amplitude than the pulse that precedes it. In the embodiment of FIG. 3, the amplitude increases linearly from one pulse to the next as shown in the first series 302, second series 304, and third series 306. Other types of changes in amplitude of individual pulses within a series are usable. For example, the pulses 400 in the embodiment depicted in FIG. 4 have a non-linear or parabolic increase in the amplitude from one individual pulse to the next as shown in the first series 402, second series 404, and third series 406. Other types of increases from one individual pulse to the next pulse within a series are usable. Furthermore, the amplitude of an individual pulse to the next pulse within a series may decrease in an analogous manner.

Figure 5:
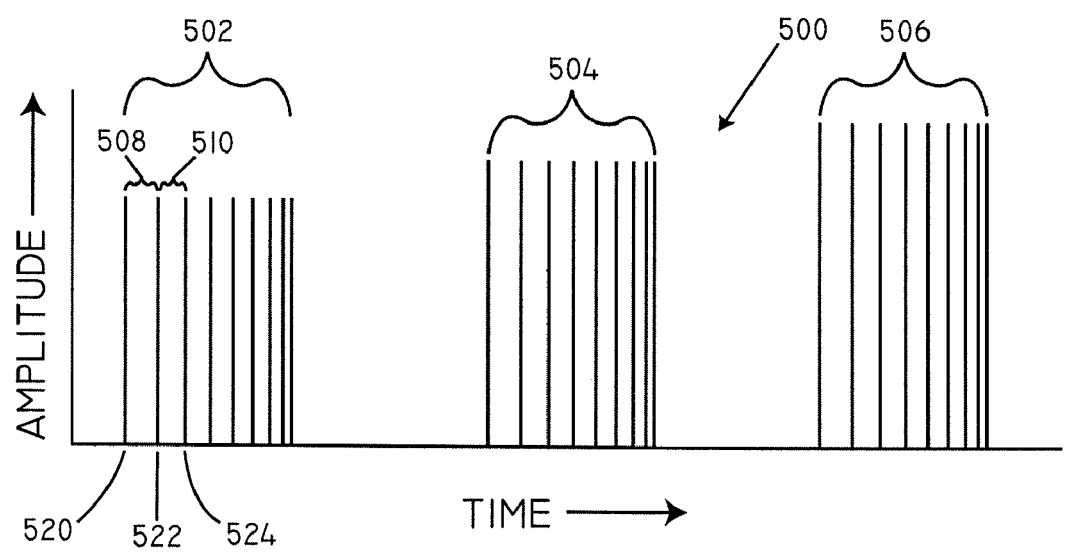
FIG. 5 is a schematic view of several series of high energy antitachycardia pacing pulses in accordance with another embodiment of the invention.

In yet another embodiment, the time interval from one individual pulse to the next individual pulse within a series may vary. For example, FIG. 5 depicts a first series 502 in which a first interval 508 is defined between a first pulse 520 and a second pulse 522. Furthermore, a second interval 510 is defined between second pulse 522 and a third pulse 524. The second time interval 510 in the depicted embodiment is shorter than the first time interval 508. As can be seen in FIG. 5, the time interval progressively decreases between the remaining individual pulses within first series 502. This pattern repeats itself in second and third series 504, 506. Other types of changes in the interval from one individual pulse to the next individual pulse within a series are usable. For example, the change in the interval may be linear or non-linear from one pulse to the next. Furthermore, the interval from one pulse to the next may increase as well as decrease.

Figure 6:
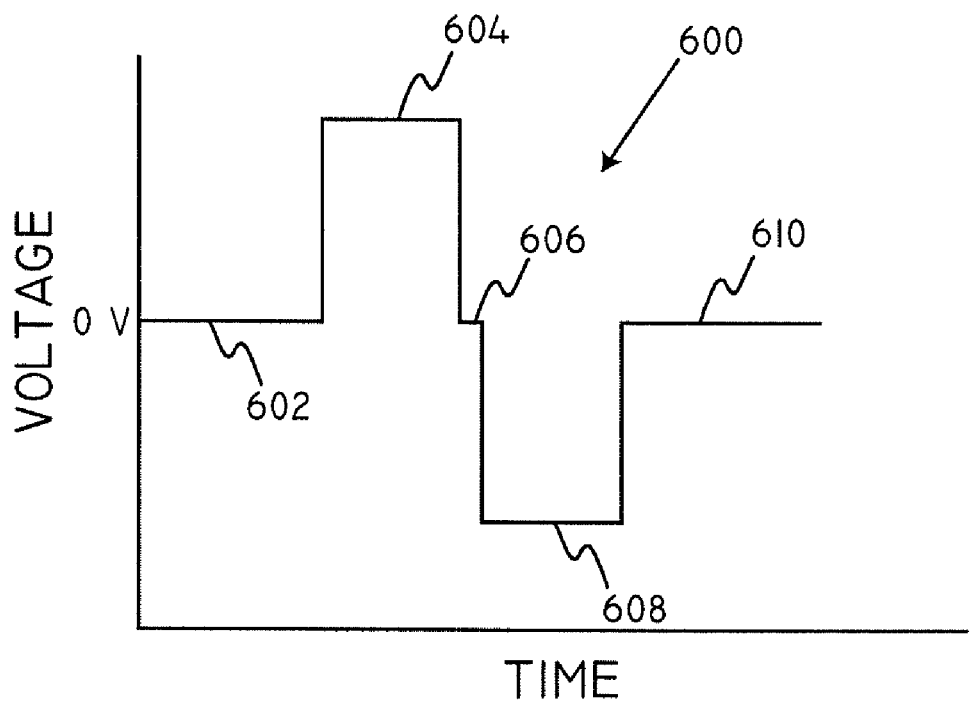
FIG. 6 is a schematic view of a biphasic pacing pulse in accordance with an embodiment of the invention.

Each individual pulse can be characterized by a waveform that defines the voltage of the pulse as a function of time. An example waveform of an individual pulse is depicted in FIG. 6. In the depicted embodiment, individual pulse 600 begins at a zero voltage state 602, as is generally the case in the time interval between individual pulses. At some point in time, generally referred to as the start of the individual pulse, the voltage of the pulse may jump to an elevated level and remain at this elevated level over a period 604. The individual pulse 600 may then be characterized by a drop in voltage. In the depicted embodiment, the voltage drops to zero and remains at zero for a finite period 606. The voltage of individual pulse 600 then drops to a reduced level, also characterized as a negative polarity, for a period 608. However, in some embodiments, the voltage will drop directly from the elevated level at the end of period 604 to the reduced level at the beginning of period 608 without having a finite period 606 at zero voltage. At the end of period 608, the voltage of the pulse 600 returns to the zero state at period 610, where it remains until the next pulse. The total length of time from the moment the pulse leaves zero voltage state 602 until it returns to the zero state at period 610 can be referred to as the "pulse width". It will be appreciated that in various embodiments herein, the pulse width can be modulated, such as made shorter or longer.

Figure 7:
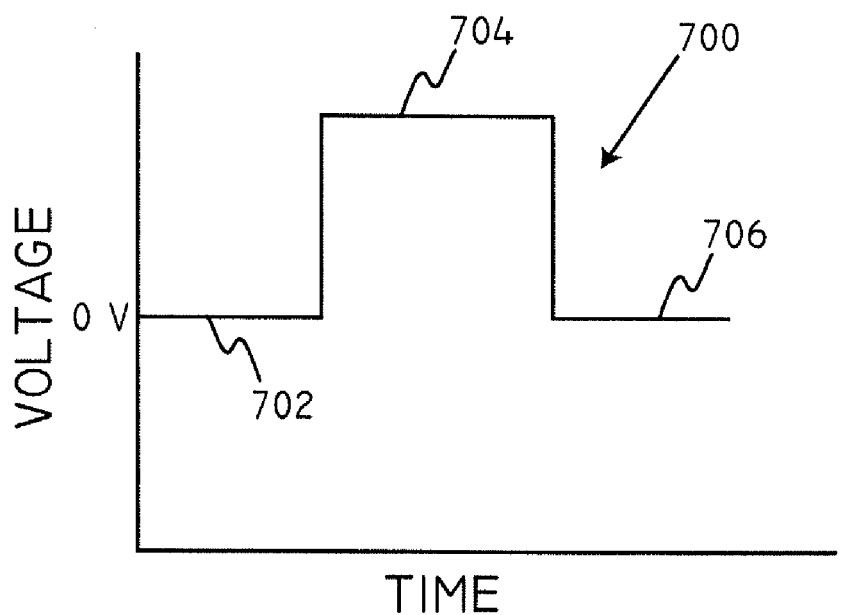
FIG. 7 is a schematic view of a monophasic pacing pulse in accordance with an embodiment of the invention.

Another embodiment of an individual pulse 700 is depicted in FIG. 7. The embodiment of FIG. 7 is similar to the embodiment of FIG. 6; however, the pulse does not include a period having a reduced voltage level. For example, the pulse 700 begins at a zero voltage state 702, which is followed by a rise to an elevated voltage level for a period 704. At the end of period 704, the voltage level drops back to the zero voltage state and remains at the zero voltage state over period 706.

Figure 8:
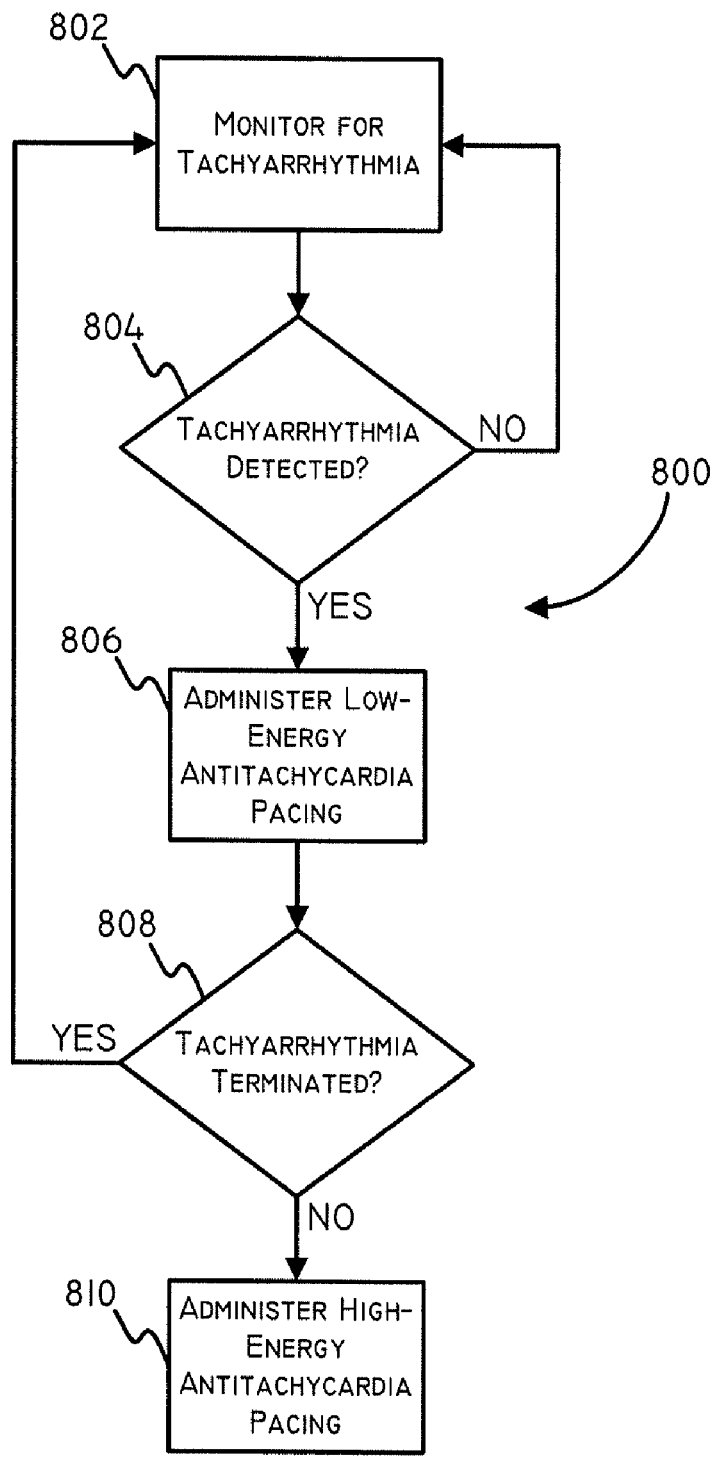
FIG. 8 is a flow chart illustrating a process in accordance with an embodiment herein.

Various methods may be configured to utilize high energy antitachycardia pulses. These various processes may, for instance, be embodied in the control module of an implantable medical device such as an implantable cardioverter defibrillator (ICD). A first example process 800 is depicted in FIG. 8. In this embodiment, various conditions of a patient are monitored to detect the presence of tachyarrhythmia at step 802. For example, various signals representing cardiac electrical activity may be monitored and these signals may be processed according to techniques known to those of skill in the art to determine whether the patient is undergoing tachyarrhythmia. For example, the device can be configured to use the signals from electrodes in order to identify myocardial electrical activity indicative of a tachyarrhythmia. The myocardial electrical activity can comprise a time-varying electrical potential. In some embodiments, the system can calculate an R-R interval time based on sensed myocardial electrical activity. In some embodiments, an R-R interval time of less than about 600 milliseconds (corresponding to a heart rate of greater than 100 beats per minute) can be indicative of a tachycardia. In some embodiments, an R-R interval time of less than about 500 milliseconds (corresponding to a heart rate of greater than 120 beats per minute) can be indicative of a tachycardia. As such, R-R interval time is one parameter that can be used as an indicator of tachycardia, either alone or in conjunction with other parameters that can also serve as indicia of tachycardia. Techniques for identifying arrhythmias from myocardial electrical activity are described in U.S. Pat. Nos. 6,658,286 and 5,301,677, for example, the content of which is herein incorporated by reference in its entirety.

At step 804, if a tachyarrhythmia is not detected, then the process returns to step 802 to continue to monitor for the presence of a tachyarrhythmia. However, if a tachyarrhythmia is detected at step 804, then the process proceeds to step 806, wherein low energy antitachycardia pacing is administered to the patient according to techniques known to those of skill in the art. At step 808, it is determined whether the tachyarrhythmia has terminated. If it has, then the process returns to step 802 to continue to monitor for a tachyarrhythmia. However, if the tachyarrhythmia has not terminated, then at step 810 high energy antitachycardia pacing is administered. This process thereby administers high energy antitachycardia pacing only if the tachyarrhythmia does not respond to low energy antitachycardia pacing. This thereby avoids unnecessarily delivering high energy antitachycardia pacing to a patient who is responsive to low energy antitachycardia pacing.

Figure 9:
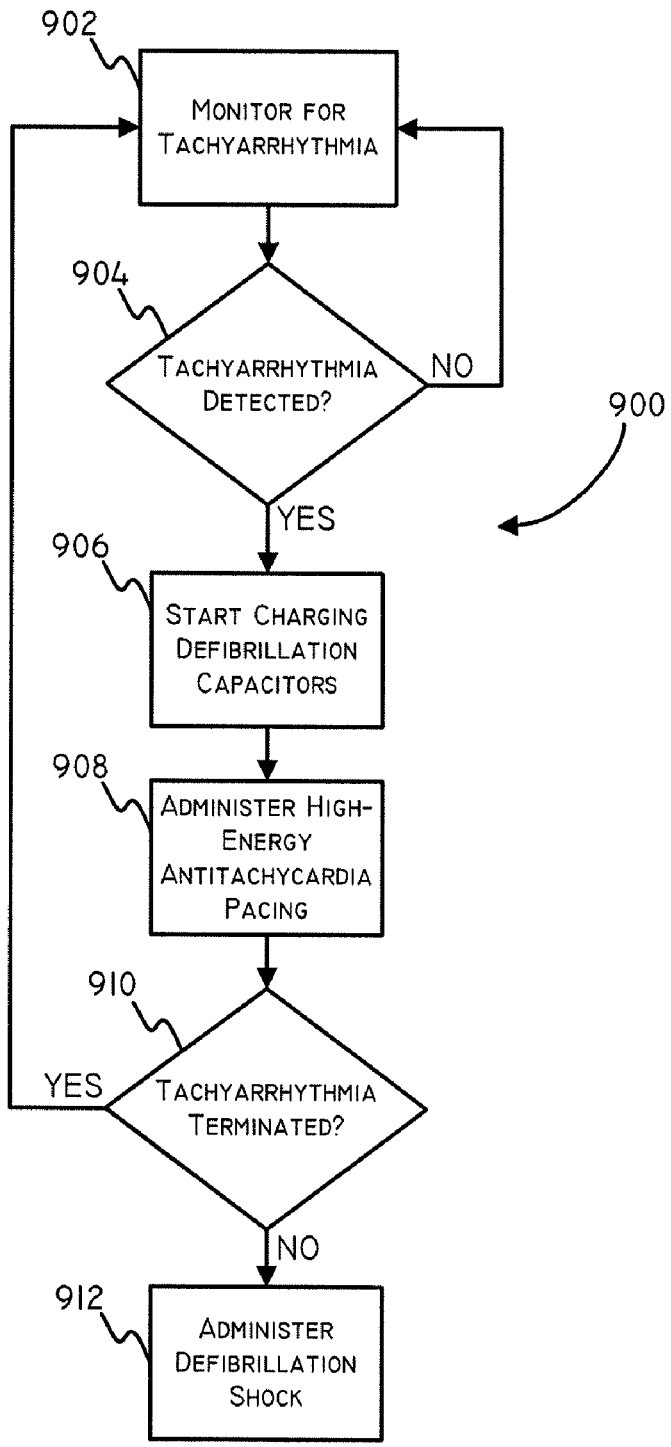
FIG. 9 is a flow chart illustrating a process in accordance with another embodiment herein.

A flow chart of another exemplary process 900 for utilizing high energy antitachycardia pacing is shown in FIG. 9. Process 900 includes step 902 of monitoring for the presence of a tachyarrhythmia. If a tachyarrhythmia is not detected at step 904, then the process returns to step 902 to continue to monitor for the presence of a tachyarrhythmia. However, if a tachyarrhythmia is detected at step 904, then at step 906 a process is initiated to begin charging defibrillation capacitors that may be present in the implantable medical device. At some point either after step 906 or simultaneous with step 906, then at step 908 high energy antitachycardia pacing is administered. At step 910, it is determined whether the tachyarrhythmia is terminated. If so, then the process 900 returns to step 902 to monitor for the presence of a tachyarrhythmia. However, if the tachyarrhythmia is not terminated, at step 912 defibrillation shocks are administered. A defibrillation shock can include an electrical stimulus delivered at voltages of greater than 200 Volts. The process described in FIG. 9 administers defibrillation shocks after it is determined that high energy antitachycardia pacing has failed to terminate the tachyarrhythmia. This technique helps increase the probability that the tachyarrhythmia will be terminated as quickly as possible.

Figure 10:
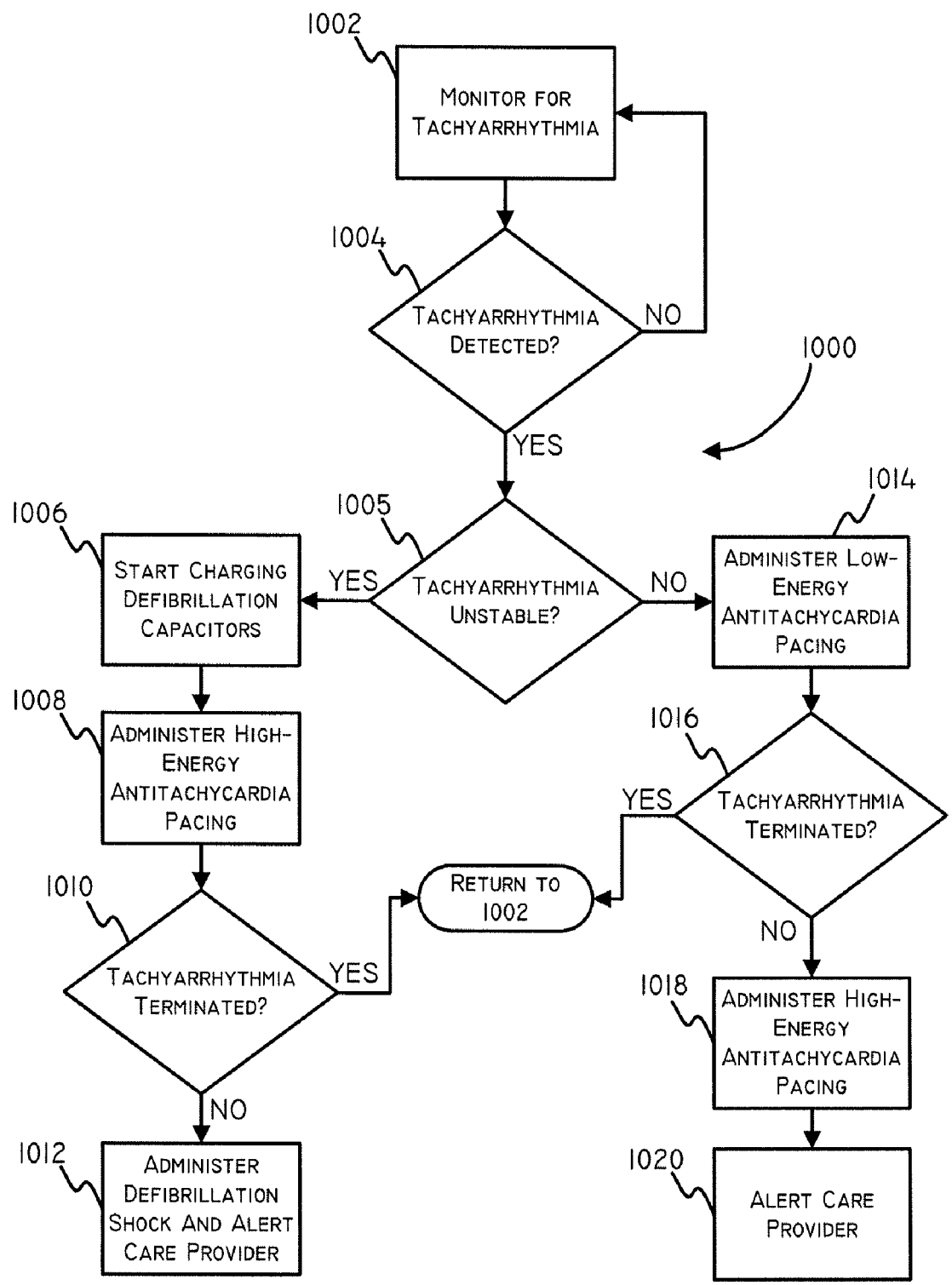
FIG. 10 is a flow chart illustrating a process in accordance with another embodiment herein.

In some cases, tachyarrhythmias may be hemodynamically unstable and it may be desirable that a process incorporate an appropriate response to an unstable tachyarrhythmia. Hemodynamically unstable tachyarrhythmias are generally more serious because by definition they are characterized by substantially reduced cardiac output. Hemodynamically unstable tachyarrhythmias can include both atrial tachyarrhythmias and ventricular tachyarrhythmias, though ventricular tachyarrhythmias are more likely to be unstable than atrial tachyarrhythmias. Process 1000 depicted in FIG. 10 includes monitoring for tachyarrhythmia at step 1002 and determining whether a tachyarrhythmia is present at step 1004. If a tachyarrhythmia is detected, at step 1005 it is determined whether the tachyarrhythmia is hemodynamically unstable.

Hemodynamic stability of a tachyarrhythmia can be assessed in various ways. For example, blood flow through the coronary venous system can be measured and if it falls below a threshold value, then the tachyarrhythmia can be deemed to be hemodynamically unstable. Another technique that can be used involves measuring pressure within the vasculature such as within the right ventricle, the pulmonary artery, the left atrium, the coronary vein, etc. In some embodiments, hemodynamic stability can be assessed using stroke impedance signals (intracardiac, cardiac component of transthoracic impedance, etc). Further techniques can include measuring blood oxygen saturation, coronary venous blood temperature, minute ventilation (MV), and assessing heart sounds.

If the tachyarrhythmia is hemodynamically unstable, then process 1000 proceeds to step 1006 and begins charging defibrillation capacitors, followed by step 1008 where high energy antitachycardia pacing is administered. At step 1010 it is determined whether the tachyarrhythmia is terminated, and if so, then the process returns to step 1002 to continue to monitor for a tachyarrhythmia. However, if the tachyarrhythmia is determined to not be terminated at step 1010, then process 1000 proceeds to step 1012 where a defibrillation shock is administered to the patient. Furthermore, step 1012 may include alerting a health care provider. Referring back to step 1005, if the tachyarrhythmia is not unstable, then process 1000 proceeds to step 1014 to administer low energy antitachycardia pacing. At step 1016 it is determined whether the tachyarrhythmia is terminated, and if so, the process 1000 returns to step 1002 to continue to monitor for tachyarrhythmia. However, if the tachyarrhythmia is not terminated, at step 1018 high energy antitachycardia pacing is administered to the patient. In some embodiments, step 1018 may be followed by step 1020 where a health care provider is alerted. Alerting a health care provider may involve transmitting a signal that is configured to be received by a health care provider, where the signal provides an indication of the medical condition of the patient.

It will be appreciated that various types of tachyarrhythmias can be treated in accordance with embodiments herein. For example, in some embodiments ventricular tachycardia can be treated. In some embodiments, supraventricular tachycardia can be treated. The high-energy anti-tachycardia therapy can be delivered to the tissue site most appropriate based on the type of tachyarrhythmia being treated. By way of example, in some embodiments, the high-energy anti-tachycardia therapy can be delivered to tissue of the right ventricle, the left ventricle, the right atrium, and/or the left atrium.

In some embodiments high energy antitachycardia therapy can be delivered to the tissue of a patient's heart at multiple sites simultaneously. For example, high energy antitachycardia therapy can be delivered to both the right atrium and the right ventricle simultaneously. As another example, high energy antitachycardia therapy can be delivered to both the right ventricle and the left ventricle simultaneously. In embodiments where such therapy is delivered to multiple sites simultaneously, the parameters of the therapy (e.g., timing, amplitude, etc.) can either be the same or can be different. For example, in some cases the amplitude of the therapy administered to the left ventricle can be higher than the amplitude of the therapy administered to the right ventricle.

Figure 11:
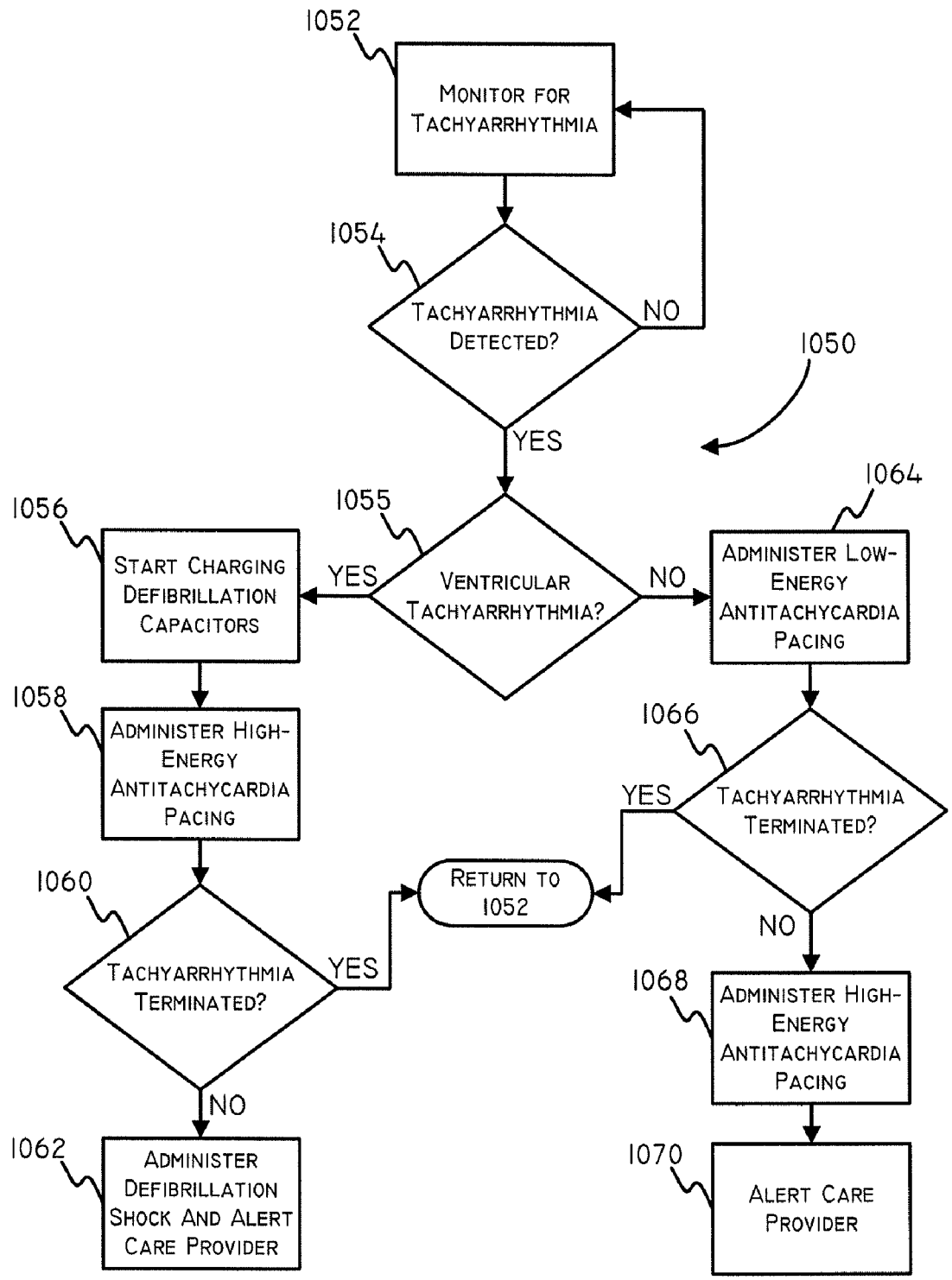
FIG. 11 is a flow chart illustrating a process in accordance with another embodiment herein.

In some cases, the system can classify the tachyarrhythmia as ventricular tachycardia or another type of tachyarrhythmia and then provide treatment accordingly. In general, ventricular tachyarrhythmias are more serious than non-ventricular tachyarrhythmias. Process 1050 depicted in FIG. 11 includes monitoring for tachyarrhythmia at step 1052 and determining whether a tachyarrhythmias is present at step 1054. If a tachyarrhythmia is detected, at step 1055 it is determined whether the tachyarrhythmia is ventricular or not. It will be appreciated that tachyarrhythmias can be discriminated using a tachyarrhythmia discrimination algorithm, for example. For example, U.S. Publ. Pat. App. Nos. 20060161069 and 20060074331, the content of both of which are herein incorporated by reference in their entirety, describe various techniques for algorithmically discriminating tachyarrhythmias.

If the tachyarrhythmia is ventricular, then process 1050 proceeds to step 1056 and begins charging defibrillation capacitors, followed by step 1058 where high energy antitachycardia pacing is administered. At step 1060 it is determined whether the tachyarrhythmia is terminated, and if so, then the process returns to step 1052 to continue to monitor for a tachyarrhythmia. However, if the tachyarrhythmia is determined to not be terminated at step 1060, then process 1050 proceeds to step 1062 where a defibrillation shock is administered to the patient. Furthermore, step 1062 may include alerting a health care provider. Referring back to step 1055, if the tachyarrhythmia is not ventricular, then process 1050 proceeds to step 1064 to administer low energy antitachycardia pacing. At step 1066 it is determined whether the tachyarrhythmia is terminated, and if so, the process 1050 returns to step 1052 to continue to monitor for tachyarrhythmia. However, if the tachyarrhythmia is not terminated, at step 1068 high energy antitachycardia pacing is administered to the patient. In some embodiments, step 1068 may be followed by step 1070 where a health care provider is alerted.

Some embodiments may utilize a tachyarrhythmia detection strategy that allows for a determination of whether the tachyarrhythmia has an origin close to a particular pacing site. For example, where a plurality of leads are placed within a patient's cardiac tissue (such as with electrodes in the right atrium, right ventricle, and/or coronary vein or left ventricle), it may be possible to determine the origin of the tachyarrhythmia based on the time at which the signal arrives at each lead. This time difference may be used to determine the relative location of the origin of the tachyarrhythmia. For example, if an electrical signal indicative of tachycardia arrives at an electrode within the right ventricle first, then it can be determined that the origin of the tachycardia is closest to that electrode.

Figure 12:
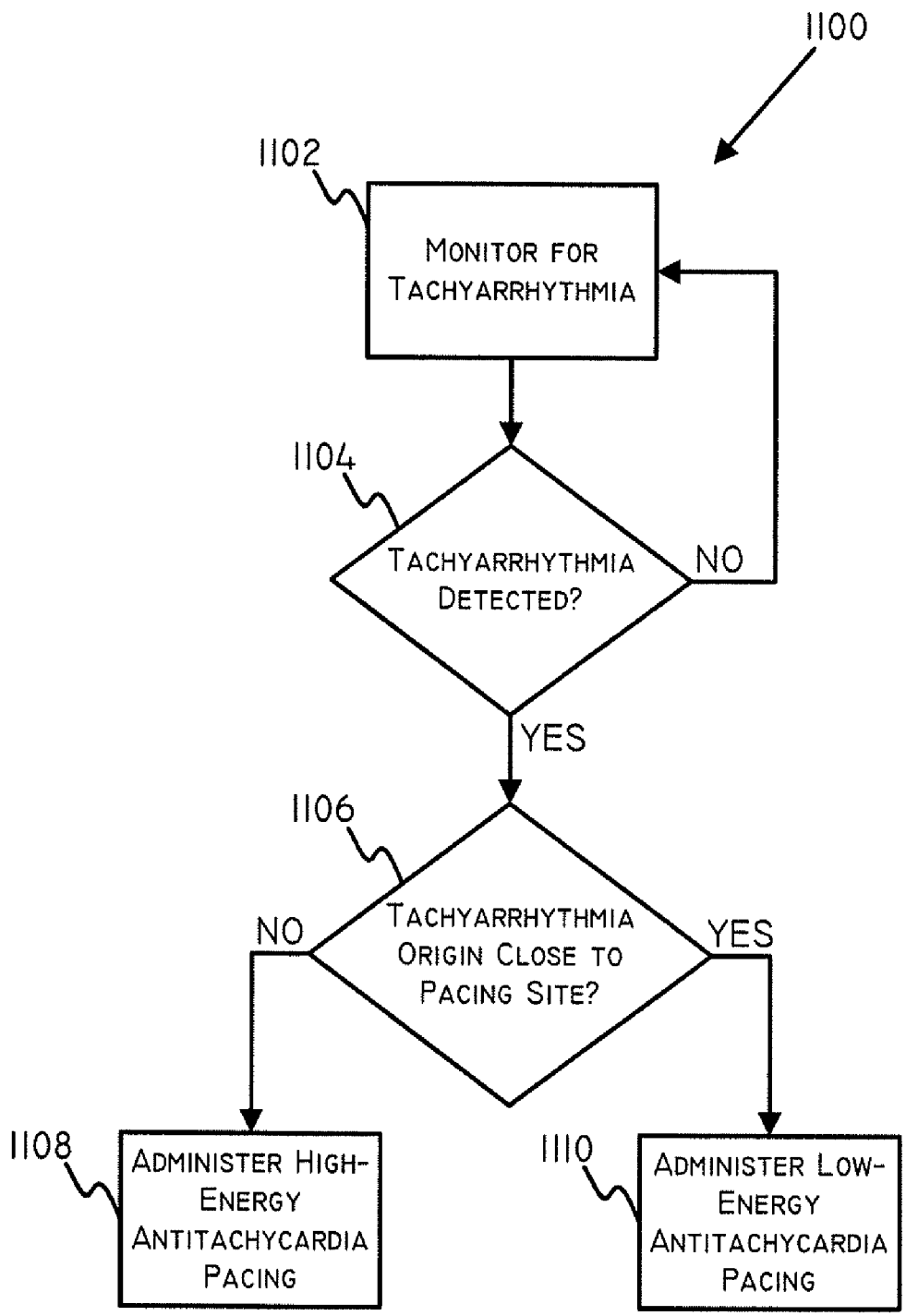
FIG. 12 is a flow chart illustrating a process in accordance with another embodiment herein.

A process 1100 can be configured to utilize this determination of the origin, as depicted in FIG. 12. For example, process 1100 may begin at step 1102 with monitoring for a tachyarrhythmia, followed by step 1104 in which it is determined whether there is a tachyarrhythmia. If there is not, then the process returns to step 1102 to continue to monitor for a tachyarrhythmia. If a tachyarrhythmia is detected, the process then proceeds to step 1106 in which it is determined whether the origin of the tachyarrhythmia is close to a particular pacing site. If the origin is close to the pacing site, then at step 1110 low energy antitachycardia pacing is administered to the patient. However, if the origin is not close to the pacing site, then at step 1108 high energy antitachycardia pacing is administered to the patient. Although not wishing to be bound by theory, it is believed that high energy antitachycardia pacing may be more effective than low energy antitachycardia pacing when the origin is relatively far from the pacing site because high energy pacing increases the effective area of tissue being stimulated.

Figure 13:
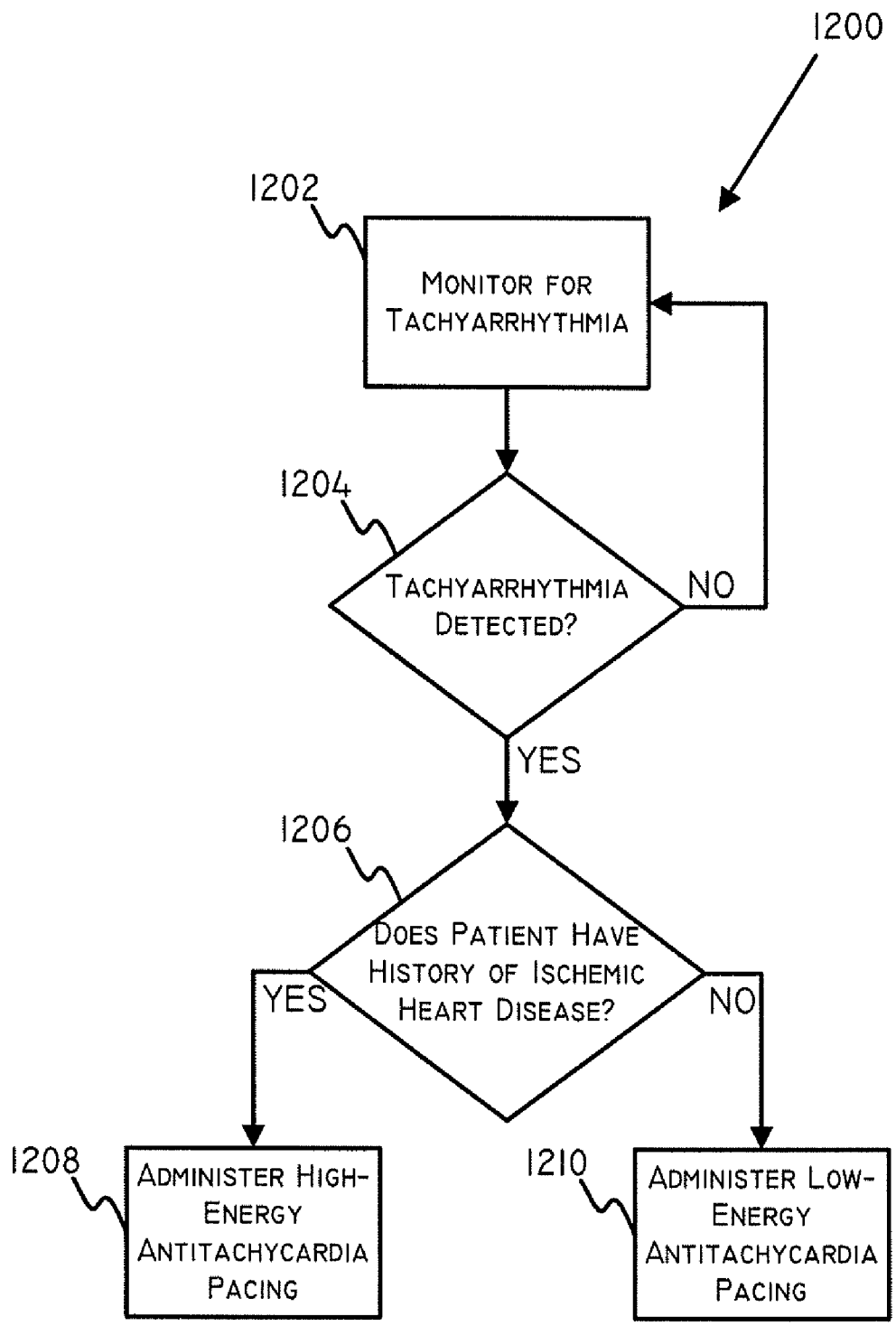
FIG. 13 is a flow chart illustrating a process in accordance with another embodiment herein.

In some embodiments, it is desirable to utilize a patient's prior medical history to determine an appropriate response to a determination that a tachyarrhythmia exists. For example, process 1200 depicted in FIG. 13 includes step 1202 in which the patient is monitored for tachyarrhythmia, and step 1204 in which it is determined whether a tachyarrhythmia exists. If a tachyarrhythmia does not exist, then process 1200 returns to step 1202 to continue to monitor for a tachyarrhythmia. However, if a tachyarrhythmia does exist, then process 1200 continues to step 1206 in which it is determined whether a patient has a history of ischemic heart disease. This step may involve, for example, checking a variable that has been stored in a memory of a device to indicate whether the patient has a history of ischemic heart disease. If the patient does not have a history of ischemic heart disease, then process 1200 progresses to step 1210 in which low energy antitachycardia pacing is administered to the patient. However, if the patient does have a history of ischemic heart disease, then at step 1208 high energy antitachycardia pacing is administered to the patient.

Figure 14:
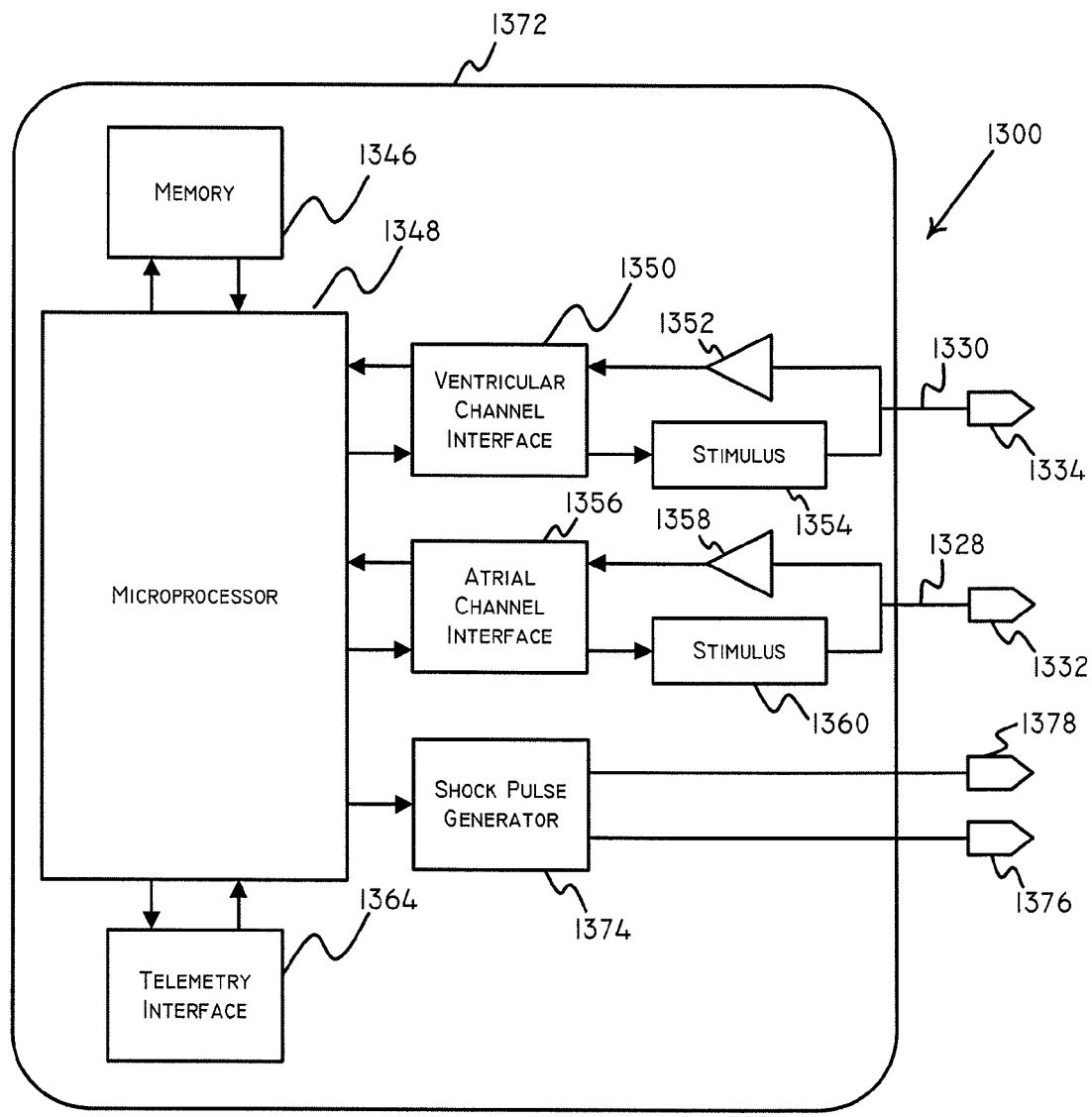
FIG. 14 is a schematic view of components of a device in accordance with various embodiments herein.

Referring now to FIG. 14, some components of an exemplary implantable system 1300 are schematically illustrated. The implantable medical system 1300 can include a controller module 1372 coupled to one or more stimulation leads 1330 and 1328. The controller module 1372 can include a microprocessor 1348 (or processor) that communicates with a memory 1346 via a bidirectional data bus. The memory 1346 typically includes ROM or RAM for program storage and RAM for data storage. The controller module 1372 can be configured to execute various operations such as processing of signals and execution of methods as described herein. A telemetry interface 1364 is also provided for communicating with an external unit, such as a programmer device or a patient management system.

The controller module 1372 can include ventricular sensing and pacing channels including sensing amplifier 1352, output circuit 1354, and a ventricular channel interface 1350 which communicates bidirectionally with a port of microprocessor 1348. It will be appreciated that in some embodiments some of the elements of the controller module 1372 shown in FIG. 14 may be omitted. Further, in some embodiments, additional elements may be included.

The ventricular sensing and pacing channel can be in communication with stimulation lead 1330 and electrode 1334. The controller module 1372 can include atrial sensing and pacing channels including sensing amplifier 1358, output circuit 1360, and an atrial channel interface 1356 which communicates bidirectionally with a port of microprocessor 1348. The atrial sensing and pacing channel can be in communication with stimulation lead 1328 and electrode 1332. For each channel, the same lead and electrode can be used for both sensing and pacing. The channel interfaces 1350 and 1356 can include analog-to-digital converters for digitizing sensing signal inputs from the sensing amplifiers and registers which can be written to by the microprocessor in order to output pulses, change the pacing pulse amplitude, and adjust the gain and threshold values for the sensing amplifiers. A shock pulse generator 1374 can also be interfaced to the microprocessor for delivering defibrillation shocks to the heart via a separate pair of electrodes 1376, 1378. In some embodiments, electrodes 1376 and 1378 can be disposed along stimulation lead 1330 and stimulation lead 1328 respectively.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A method of treating a tachyarrhythmia comprising:
   administering a first series of electrical pulses to a patient with an implantable medical device, the first series comprising three or more electrical pulses, the electrical pulses comprising an amplitude of greater than 8 Volts and less than 40 Volts, the first series of electrical pulses having an interval of less than about 600 ms in between individual pulses; and
   wherein each of the electrical pulses of the first series increase in amplitude between the first electrical pulse of the first series and the last electrical pulse of the first series.

2. The method of claim 1, wherein the electrical pulses of the first series increase non-linearly in amplitude between the first electrical pulse of the first series and the last electrical pulse of the first series.

3. The method of claim 1, wherein the electrical pulses of the first series increase parabolically in amplitude between the first electrical pulse of the first series and the last electrical pulse of the first series.

4. The method of claim 1, the first series comprising between three and eight electrical pulses.

5. The method of claim 1, further comprising administering a second series of electrical pulses.

6. The method of claim 1, wherein each electrical pulse is biphasic.

7. The method of claim 1, further comprising monitoring for the presence of a tachyarrhythmia.

8. The method of claim 1, further comprising classifying the tachycardia as either sinus tachycardia, supraventricular tachycardia, or ventricular tachycardia based on sensed myocardial electrical activity, wherein the first series of electrical pulses are only administered if the tachycardia is classified as either supraventricular tachycardia or ventricular tachycardia.

9. The method of claim 1, wherein the initial interval between successive electrical pulses within the first series of electrical pulses is about 80% of the R-R interval of the tachyarrhythmia to be treated.

10. The method of claim 1, further comprising timing delivery of the first series to be delivered during a refractory period.

11. The method of claim 1, further comprising determining whether the origin of the tachyarrhythmia is close to a particular pacing site.

12. A method of treating a tachyarrhythmia comprising:
    administering a first series of electrical pulses to a patient with an implantable medical device, the first series comprising between three and eight electrical pulses, the electrical pulses comprising an amplitude of between 10 Volts and 30 Volts, the first series of electrical pulses having an interval of less than about 600 ms in between individual pulses; and
    wherein each of the electrical pulses of the first series increase in amplitude between the first electrical pulse of the first series and the last electrical pulse of the first series.

13. The method of claim 12, wherein the electrical pulses of the first series increase non-linearly in amplitude between the first electrical pulse of the first series and the last electrical pulse of the first series.

14. The method of claim 12, wherein the electrical pulses of the first series increase parabolically in amplitude between the first electrical pulse of the first series and the last electrical pulse of the first series.

15. The method of claim 12, further comprising timing delivery of the first series to be delivered during a refractory period.

16. The method of claim 12, further comprising determining whether the origin of the tachyarrhythmia is close to a particular pacing site.

* * * * *